United States Patent [19]

Miyazaki et al.

[11] Patent Number: 4,873,261

[45] Date of Patent: Oct. 10, 1989

[54] PHARMACEUTICAL COMPOSITION FOR TREATING ULCERATIVE LARGE INTESTINAL DISEASE

[75] Inventors: Wasei Miyazaki; Yasuhiko Inoue, both of Tokushima, Japan

[73] Assignee: Otsuka Pharmaceutical Co., Ltd., Tokyo, Japan

[21] Appl. No.: 154,205

[22] Filed: Feb. 10, 1988

[30] Foreign Application Priority Data

Feb. 13, 1987 [JP] Japan .................................. 62-32129

[51] Int. Cl.$^4$ ............................................ A61K 31/34
[52] U.S. Cl. ...................................... 514/462; 514/925
[58] Field of Search ......................................... 514/462

[56] References Cited

U.S. PATENT DOCUMENTS 4,229,466  10/1980  Miyazaki et al. ................... 514/462

Primary Examiner—Frederick E. Waddell
Attorney, Agent, or Firm—Finnegan, Henderson, Farabow, Garrett & Dunner

[57] ABSTRACT

A method for treating ulcerative large intestinal diseases with a pharmaceutical composition containing, as the active ingredient, a sesquiterpene compound or a salt thereof.

2 Claims, 3 Drawing Sheets

× 40

× 100

× 100

× 40

×100

×40

PHARMACEUTICAL COMPOSITION FOR TREATING ULCERATIVE LARGE INTESTINAL DISEASE

FIELD OF THE INVENTION

The present invention relates to a pharmaceutical composition for treating ulcerative large intestinal diseases, such as ulcerative colitis and other diseases.

PRIOR ART AND PROBLEMS INVOLVED THEREIN

Ulcerative colitis is one of the chronic inflammatory bowel diseases which are caused by unknown origin, and are called as spontaneous inflammatory bowel diseases (IBD) together with Crohn disease. The ulcerative colitis is a disease by which the mucosa of large intestine is attacked, and sometimes erosions and ulcers are formed on the mucosa. In most of the cases, once said diseases begun at the rectum as well as at the sigmoid colon, then the diseases are repeatedely appearing in the limited areas with recurrences and remissions, and there are observed the cases of ascending developments and the cases in that the whole portions of the large intestine are attacked from the beginning of the diseases.

At the moment, neither method for curing nor method for preventing recurrence of the above-mentioned ulcerative large intestinal diseases are available, because no causal treatment has been established yet, since the diseases are caused by unknown origin.

On the other hand, as to effective drugs for introducing remissions of various symptoms caused by the above-mentioned ulcerative large intestinal diseases, there are known some of immunosuppressive agents, for example adrenocortical steroids, ACTH (adrenocortical stimulating hormone), Salazopyrin (salicylazosulfapyridine; SASP), 6-MP (6-mercaptopurine) and derivatives thereof, such as Imuran (Azathioprine) and the like, thus, there have been established chemotherapies by using these immunosuppressive agents as interal medicinal therapies. However, when administering the above-mentioned agents for long period of time, there are observed certain side-effects , for example diseases in the digestive systems such as nausea, vomiting, anorexia and the like, as well as generalized symptoms such as headache, dizziness, malaise, eruption and the like. In addition to the above, when the administration of the above-mentioned agents were stopped, there are observed higher ratio of recurrence of ulcerative bowel diseases and also sufficient effects of remissions can not be expected. Furthermore, the above-mentioned agents only possess poor effect in rapid actions as well as involve unfavorable problems, thus these immunosuppressive agents are in the stage of re-evaluation. Under the circumstances, the establishment of radical therapy including the research and developments of novel drugs to be substituted for the above-mentioned immunosuppressive agents for treating ulcerative large intestinal diseases are keenly desired.

MEANS FOR SOLVING THE PROBLEMS

An object of the present invention is to provide novel pharmaceutical compositions for treating ulcerative large intestinal diseases, such as ulcerative colitis.

Another object of the present invention is to provide a method for treating ulcerative large intestinal diseases, such as ulcerative colitis.

BRIEF EXPLANATION OF THE DRAWINGS

The accompanied

DETAILED EXPLANATION OF THE INVENTION

Figure 1:
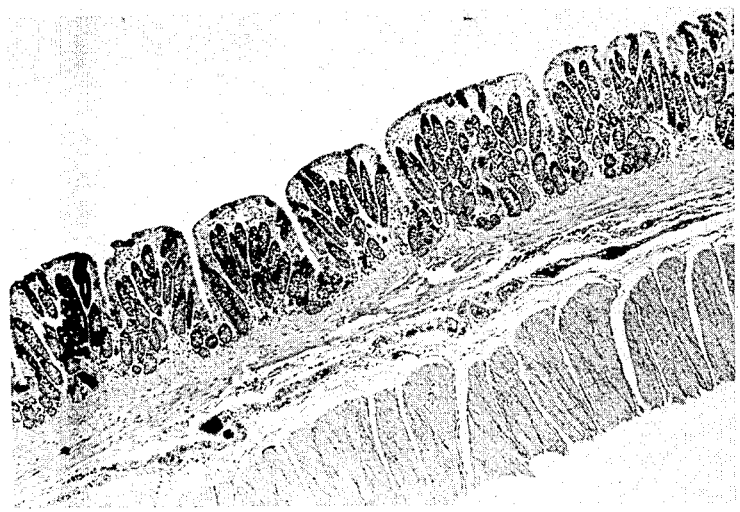
FIG. 1 to FIG. 6 are microscopic photographs of tissues of the large intestine of rabbits used in the tests for curing ulcerative large intestinal diseases according to the Pharmacological Test - 1.

According to the present invention, a pharmaceutical composition for treating ulcerative large intestinal diseases containing, as the active ingredient, at least one of the analogous compounds of sesquiterpene or salt thereof represented by the formula, selected from the group consisting of the formula (1),

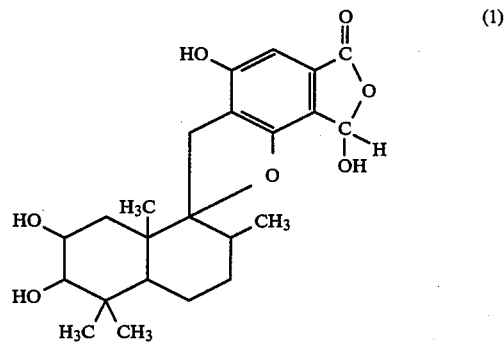

and the formula (2),

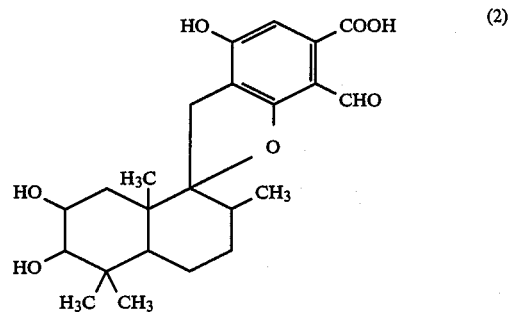

can be provided.

Furthermore, according to the present invention, method for treating ulcerative large intestinal diseases by administering at least one of the analogous compounds of sesquiterpene or salt thereof represented by the formula, selected from the group consisting of the formula (1) and formula (2) as mentioned above can be provided.

Sesquiterpene compounds or salt thereof represented by the formula (1) and (2) used as the active ingredient in the pharmaceutical composition according to the present invention, said compounds have been found and developed by the present inventors, and they are disclosed in the specification of German Patent No. DE 2821403, corresponding to U. K. Patent Specification No. 1601479 and Japanese Patent Kokai (Laid-open) No. 54-36255 (1979) and in the specification of German Patent Offenlegungsschrift No. DE 3031788, corresponding to Japanese Patent Kokai (Laid open) No.

54-37832 (1979). These prior art references disclose in that the above-mentioned sesquiterpene compounds are useful in some other pharmaceutical applications.

According to an extensive study made by the present inventors, which were quite different from the applications disclosed in the above-mentioned prior art references, the present invention was successfully established by the finding in that the sesquiterpene compounds represented by the formula (1) and (2) are useful for treating ulcerative large intestinal disease, particularly they are useful for treating ulcerative colitis, such pharmacological activities could not have been anticipated from the pharmacological applications disclosed in the above-mentioned prior art references.

When crystals of compounds represented by the formula (1) are dissolved in a solvent, especially in a basic solvent, the compounds id converted into an equilibrium mixture containing a carboxylic acid represented by the formula (2) which is a tautomeric isomer of the compound of the formula (1). Thus, according to time sequential determination of NMR spectrum analysis, 20 minutes after the dissolution of a compound of the formula (1) in dimethyl sulfoxide, there are determined a peak of the significant signal for a lactol of 6.36 ppm, also determined a peak of the significant signal for an aldehyde proton (—$\overline{CHO}$) of 9.89 ppm. The ratio of integrations of both peak of signals is about 73 of the former to about 27 of the latter. Then, 2 hours after the dissolution, the peak of signal of 9.89 ppm further increased, and the ratio of integrations of both signals reaches to 70:30, and this ratio of integrations of both signals on the NMR analytical chart would not be changed any more even though 63 hours after the dissolution of compound of the formula (1). In other words, compound of the formula (2) exists in the ratio of 3:7 against compound of the formula (1) in the above-mentioned equilibrium mixture prepared by dissolving a compound of the formula (1) in said solvent.

Thus, said equilibrium mixture of compound of the formula (1) with compound of the formula (2) can be used as the active ingredient to be contained in a pharmaceutical composition for treating ulcerative large intestinal diseases according to the present invention.

It should be noted the fact, however that, compound of the formula (2) which is a tautomeric isomer of compound of the formula (1) cannot be formed when methanol or pyridine is used as the solvent.

Similar to each of these compounds of formula (1) and (2) as well as the equilibrium mixture of both compounds to be contained as the active ingredient, a pharmaceutical composition according to the present invention may contain, as the active ingredient, salt or salts of basic compounds of each of these tautomeric isomers of compounds of the formula (1) and (2). The above-mentioned salt or salts of basic compounds of each of these tautomeric isomers of compounds of the formula (1) and formula (2) may be obtained by reacting the acidic groups in compounds (1) and (2), thus at least one of the functional groups of the phenolic hydroxyl group in compound of the formula (1) and the carboxylic acid which constitutes the lactol ring of compound of the formula (2), with a basic compound. As to the basic compounds to be used in preparation of such salts, the examples including hydroxides, carbonates of alkali metals and alkaline earth metals, for example, sodium hydroxide, potassium hydroxide, calcium hydroxide, sodium carbonate, potassium carbonate, sodium bicarbonate or the like. In addition to the above, organic amines such as methylamine, ethylamine, isopropylamine, morpholine, piperazine, piperidine, 3,4-dimethoxyphenethylamine and the like can also be used as the abovementioned basic compounds.

Furthermore, each of compounds of the formulas (1) and (2) to be contained as the active ingredient in a pharmaceutical composition according to the present invention include their stereo isomers, thus the present invention also inevitably includes the use of said stereo isomers of these compounds of the formulas (1) and (2).

A pharmaceutical composition for treating ulcerative large intestinal diseases according to the present invention can practically be applied in the form of a pharmaceutical compositions by using pharmaceutically acceptable carriers which are commonly used with the active ingredients. As to the pharmaceutically acceptable carriers, which are commonly used depend on various preparation forms, any type of diluents or excipients such as fillers, bulking agents, binding agents, wetting agents, disintegrating agents, surface active agents, lubricating agents and the like can be exemplified. These diluents or excipients can preferably be selected depend on the desired administration unit forms.

Administration unit forms of pharmaceutical composition according to the present invention can be selected from widely, depend on various therapeutic purposes, and as the typycal unit forms, the examples including tablets, pills, powders, liquids, suspensions, emulsions, granules, capsules, supositories, injections (solutions and suspensions) and ointments and the like. In case of preparing the tablets, they can be prepared by using excipients for example, lactose, white sugar, sodium chloride, glucose, urea, starch, calcium carbonate, kaoline, crystalline cellulose and silicic acid; binding agents for example water, ethanol, propanol, simple syrup, glucose solutions, starch solutions, gelatin solutions, carboxymethyl cellulose, shelac, methyl cellulose, potassium phosphate, polyvinyl pyrrolidone and the like; disintegrating agents for example dried starch, sodium alginate, agar-agar powder, laminalia powder, sodium bicarbonate, calcium carbonate, esters of polyoxyethylene sorbitan fatty acids, sodium laurylsulfate, stearic acid monoglyceride, starch, lactose and the like; disintegration inhibiting agents for example white sugar, stearin, coconut butter, hydrogenated vegetable oils and the like; absorption promotor for example quaternary ammonium basis, sodium laurylsulfate and the like; wetting agent for example glycerin, starch and the like; adsobing agents for example starch, lactose, kaoline, bentonite, colloidal silicic acid and the like; lubricants for example purified talc, stearates, boric acid, polyethylene glycols and the like. If necessary, the tablets can be further coated with usual coating materials to make them into coated tablets, for example tablets coated with sugar, tablets coated with gelatin film, tablets coated with enteric coating layers, tablets coated with films or double layer tablets as well as multiple layer tablets, and the like. In case of preparing the pills, any carrier which is known and used widely in this field can be used, for example, excipients such as glucose, lactose, starch, coconut butter, hydrogenated vegetable oils, kaoline, talc and the like; binding agents such as gum arabi powder, tragacanth gum powder, gelatin, ethanol and the like; disintegrating agents such as laminalan, agar-agar and the like. In case of preparing the suppositories, any carrier which is known and used widely in this field can be used, for example, polyethylene glycols, coconut butter, higher alcohols, esters of higher alcohols, gelatin, semi-synthesized glyceride and the like. In case of preparing the capsules, compounds of the formula (1) or (2) to be contained as the active ingredient in pharmaceutical composition according to the present invention, or salts thereof are admixed with the above-mentioned carriers and the thus obtained mixture is filled in a solid gelatin capsules or soft capsules. In case of preparing the injection preparations such as liquids, emulsions, suspensions and the like prepared are further sterilized and are preferably isotonic to the blood. As to the diluents, water, ethyl alcohol, propylene glycol, ethoxylated isostearyl alcohol, polyoxylated isostearyl alcohol, polyoxyethylene sorbitan fatty acid esters and the like can be used. In these instances, adequate amounts of sodium chloride, glucose or glycerin may be added to make the desired injection preparations isotonic. Furthermore, usual dissolving auxiliaries, buffer solutions, analgesic agents may be added in the desired injectable preparations. Also, coloring materials, preservatives, perfumes, seasoning agents, sweetening agents and other medicines may be added in the desired pharmaceutical preparations.

The amount of compounds of the formula (1) and/or of the formula (2) and salts thereof to be contained as the active ingredient in pharmaceutical composition for treating ulcerative large intestinal diseases according to the present invention is not specifically restricted, and can suitably be selected from a wide range, and generally 0.5 to 30% by weight of the compound or salt thereof may be contained in the whole composition.

Methods for administering the pharmaceutical composition for treating ulcerative large intestinal diseases according to the present invention are not specifically restricted, thus the composition can be administered in various forms of pharmaceutical preparations depend on the age of patient, the distinction of sex, the degree of symptoms and other conditions of the patient. For example, tablets, pills, solutions, suspensions, granules and capsules are administered orally; injection preparations are administered intraveneously singly, or administered with usual injectbale transfusions such as glucose solutions, amino acid solutions and the like, if necessary, the injection preparations are administered singly intramuscularly, intracutaneously, subcutaneously or intraperitoneally. The suppositories are administered into rectum.

The dosage of the pharmaceutical composition according to the present invention can be selected suitably according to the methods for administrations, the age of patient, the distinction of sex and other conditions as well as the degree of the symptoms, and generally 0.1 mg to 50 mg/body/day of the active ingredient may be administered, and the pharmaceutical composition may be administered in 1 to 4 times/day.

Examples of preparation of the active ingredients to be contained in the pharmaceutical compositions according to the present invention and Examples of the pharmaceutical composition containing said active ingredient are illustrated below. Examples of preparation of the active ingredients are conducted by procedures according to the disclosures in Japanese Patent Kokai (Laid-open) No. 54-36255 (1979).

EXAMPLE 1

A 500 ml Sakaguchi flask was charged with 100 ml of a culture medium of the following formulation, and *Stachybotrys complementi* nov. sp. K-76 (FERM No. 3801, deposited in Fermentation Research Institute, Japan) was cultivated at 28° C. and a pH of 6 for 4 days under reciprocating shaking condition.

| Formulation of Culture Medium | |
|---|---|
| Glycerol | 0.5% |
| Starch | 1.0% |
| Lactose | 0.2% |
| Soybean powder | 0.5% |
| Yeast extract | 0.1% |
| Malt extract | 0.2% |
| $CaCO_3$ | 0.3% |
| $MgSO_4$ | 0.05% |

A 30-liter jar fermentor was charged with 20 liters of a culture medium of the above formulation, and one flask of the resulting seed culture was cultivated in the culture medium at 28° C. for 5 days with stirring at 300 rpm at an aeration rate of 1 liter per liter of the culture medium per minute. The resulting culture broth was centrifuged at a speed of 8000 rpm to remove the microbial cells. To the supernatant liquid was added 5 liters of methanol, and the mixture was stirred and then allowed to stand for 3 hours. The mixture was centrifuged and the solid material was removed. The supernatant was extracted with an equal quantity by volume of ethyl acetate. The solvent of the ethyl acetate layer was removed by evaporation under reduced pressure. The residue thus obtained was dissolved in methanol, and passed through a column of activated carbon. The eluate was concentrated to dryness under reduced pressure. The dried mass was dissolved in a mixture of chloroform and ethyl acetate (1:1, v/v) and then the solution was gel-filtered through a column of Sephadex LH-20. The filtrate was subjected to thin-layer chromatography [using a mixture of ethyl acetate/chloroform/acetic acid (volume ratio of 50:50:2) as a developing solvent], and a fraction having an anticomplement activity corresponding to Rf=0.34 was collected. Alternatively the filtrate was subjected to thin-layer chromatography [using a mixture of benzene/butanol/acetic acid (volume ratio of 60:15:5) as a developing solvent], and a fraction having an anti-complement activity corresponding to Rf=0.58 was collected. The solvent was removed by evaporation from the fraction yielded 2.0 g of 6,7-dihydroxy-2,5,5,8a-tetramethyl-1,2,3,4,4a,5,6,7,8,8a-decahydronaphthalene-1 spiro-2'-(6',7'-diformyl-4'-hydroxy-2',3'-dihydrobenzofuran) as a light yellow weakly acidic substance having an anti-complement activity. Formation of this substance was confirmed by the following physicochemical characteristics.

(1) Refractive index: $[\alpha]_D^{20} = -48°$ (c = 2.5, methanol)
(2) Elemental analysis value for $C_{23}H_{30}O_6$:
    Calculated (%): C 68.64, H 7.51
    Found (%): C 68.58, H 7.55
(3) Ultraviolet absorption spectrum (UV) analysis:
    $\lambda_{max}^{Ethanol} = 246$ nm ($\epsilon = 16474$)
    $= 307$ nm ($\epsilon = 6659$)

EXAMPLE 2

2.1 Grams of silver nitrate was dissolved in 1 ml of water, and 3.5 ml of a 5.8 M aqueous solution of sodium hydroxide was added thereto. The mixture was stirred at room temperature for 20 minutes. Then, a solution of 1.0 g of 6,7-dihydroxy-2,5,5,8a-tetramethyl-1,2,3,4,4a,5,6,7,8,8a-decahydronaphthalene-1-spiro-2'-(6',7'-diformyl 4'-hydroxy2',3'-dihydrobenzofuran) obtained as described in Example 1 in 3 ml of ethanol was added thereto. The reaction mixture was stirred at room temperature for 1.5 hours, and the pH was adjusted to about 2 with 2N hydrochloric acid. The reaction mixture was extracted with the same quantity by volume of 5 ethyl acetate, and the solvent in the extract was removed by evaporation under reduced pressure. The residue thus obtained was purified by means of a silica gel column chromatography [silica gel: "Wako C-200", a product of Wako Pure Chemicals, Co., Ltd., eluent: chloroform/ethyl acetate/acetic acid (100:50:2 by volume)]. A fraction corresponding to Rf=0.37 by thin-layer chromatography [using a mixture of ethyl acetate/chloroform/acetic acid (50:50:2 by volume) as a developing solvent], or a fraction corresponding to Rf=0.71 by thin-layer chromatography [using a mixture of benzene/butanol/acetic acid (60:15:5 by volume) as a developing solvent] was collected. The solvent was removed by evaporation from the fraction, yielded 700 mg of 4,8-dihydroxy-6-oxo-2,3,6,8-tetrahydro-furo[3,4-g]benzofuran-2-spiro-1'-(6',7'-dihydroxy-2',5',5',8'a-tetramethyl-1',2',3',4',4'a,5',6',7',-8',8'a-decahydronaphthalene) as a light yellow indefinite form of crystals. The compound had the following physico-chemical properties, and the formation of this compound was confirmed by these properties.

(1) Refractive index: $[\alpha]_D^{20} = -44.8°$ (c = 0.9 methanol)
(2) Elemental analysis value for $C_{23}H_{30}O_7$:
  Calculated (%): C 66.03, H 7.18
  Found (%): C 65.93, H 7.21

EXAMPLE 3

To a mixture of 5 ml of a 0.4N aqueous solution of sodium hydroxide and 5 ml of ethanol was added 418 mg of 4,8-dihydroxy-6-oxo-2,3,6,8-tetrahydro-furo[3,4-g]benzofuran-2-spiro-1'-(6'7'-dihydroxy-2',5',5',8'a-tetramethyl-1',2',3'4',4'a5',6',7',8',8'a-decahydronaphthalene). The reaction mixture was stirred at 30 to 40° C. for 30 minutes under a stream of nitrogen gas. After the reaction, the solvent was removed by evaporation under reduced pressure, and the residue was dried. To the residue was added 10 ml of acetone, and the acetone-soluble portion was removed by filtration. The resulting crude crystals were recrystallized from water/acetone to yield 342 mg of disodium 6,7-dihydroxy-2,5,5,8a-tetramethyl-1,2,3,4,4a,5,6,7,8,8a-decahydronaphthalene-1-spiro-2'-(6'-carboxylate-7'-formyl-4'-oxide-2',3'-dihydrobenzofuran) as a light yellow indefinite crystals. The compound had the following physico-chemical properties, and the formation of this compound was confirmed by these properties.

(1) Refractive index: $[\alpha]_D^{20} = -44.2°$ (c = 1.25, $H_2O$)
(2) Elemental analysis value for $C_{23}H_{28}O_7Na_2$:
  Calculated (%): C 59.74, H 6.10
  Found (%): C 59.48, H 5.91
(3) Ultraviolet absorption spectrum (UV) analysis:
  $\lambda_{max}^{H_2O}$ = 252 nm ($\epsilon$ = 20500)
     = 330 nm ($\epsilon$ = 45900)

In carrying out the above-mentioned Example 3, when an equimolar quantity, generally 1.2 times the molar quantity of sodium hydroxide is used to the starting compound, there can be obtianed a monosodium salt of the carboxylic group of said compound.

| Example of pharmaceutical composition - 1 | |
|---|---|
| Compound prepared in Example 3 | 5 mg |
| Glucose | 250 mg |
| Distilled water for injection | q.s. |
| Total amount | 5 ml |

Compound prepared in Example 3 and glucose were dissolved in distilled water for injection, then the solution was poured into a 5 ml ampoule, the air in the ampoule was purged with nitrogen gas, and the ampoule was sterilized at 121° C. for 15 minutes to obtain an injectable preparation of a pharmaceutical composition for treating ulcerative large intestinal diseases according to the present invention.

| Example of pharmaceutical composition - 2 | |
|---|---|
| Compound prepared in Example 2 | 5 mg |
| Semi-synthetic glyceride base | q.s. |
| Total amount | 500 mg |

Compound prepared in Example 2 was added to the semi-synthetic glyceride base, and they were mixed and suspended at 50° C. The mixture was cast into a mold, and allowed to cool naturally, and removed from the mold, thus a pharmaceutical composition for treating ulcerative large intestinal diseases according to the present invention was obtained in the form of suppository.

| Example of pharmaceutical composition - 3 | |
|---|---|
| Compound prepared in Example 3 | 5 g |
| Avicel | 120 g |
| (a trademark for microcrystalline cellulose, manufactured by Asahi Chemical Industry, Co., Ltd.) | |
| Corn starch | 90 g |
| Magnesium stearate | 6 g |
| TC-5 | 10 g |
| (a trademark for hydroxypropylmethyl cellulose, manufactured by The Shin-Etsu Chemical Co., Ltd.) | |
| Polyethylene glycol-6000 | 3 g |
| Castor oil | 40 g |
| Ethanol | 40 g |

Compound prepared in Example 3, Avicel, corn starch and magnesium stearate were mixed and ground, then the mixture was tableted by using a conventional pounder (R 10 mm) for sugar coating. The resulting tablets were coated with a film coating agent composed of TC-5, polyethylene glycol 6000, castor oil and ethanol to produce a pharmaceutical composition for treating ulcerative large intestinal diseases in the form of film-coated tablets.

Pharmacological tests of the active ingredients to be contained in pharmaceutical compositions for treating ulcerative large intestinal diseases according to the present invention and the results obtained from the tests are explained as follows.

Pharmacological Test - 1

(Test for evaluating the effects of curing ulcerative large intestinal diseases)

The test was conducting by procedures according to an article written by Kitano, et al. [A. Kitano, K. Kobayashi, H. Oshiumi, K. Ookawa, S. Oka, Y. Tanaka, S. Kuwajima, and T. Ono: J. J. Gastroenterol., 78, (11), pp. 2104-2111, (1981)]by using matured male rabbits (average body weight: 2.2 kg) as test animals. The test animals were sensitized by subcutaneously administered with 1% of an aqueous solution of λ-degraded carrageenan (manufactured by Wako Pure Chemicals Co., Ltd.). One (1) week after the sensitization, each of the test compounds (the active ingredients to be contained in the pharmaceutical composition according to the present invention) was administered to the test animals.

The test animals were grouped into six (6) test groups, i.e., Group I through Group VI as follows.

(a) Group I (A group of the test animals to which only λ-degraded carrageenan were administered)

This group consists of four (4) test animals to which the above-mentioned 1% of an aqueous solution of λ-degraded carrageenan were orally administered as a drinking water every day, for 8 or 16 weeks.

(b) Group II (A group of the test animals to which λ-degraded carrageenan together with the active ingredient were administered orally simultaneously)

This group consists of three (3) test animals to which 1% of an aqueous solution of λ-degraded carrageenan, contianing the compound prepared in Exmaple 3 as the active ingredient, were orally administered as a drinking water every day, for 8 or 16 weeks. The amount of said active ingredient being contained in the drinking water was adjusted to 0.1 mg/kg/day, so as to be administered to one test animal in average 0.2 mg.

(c) Group III (A group of the test animals to which the drinking water used in Group I and that used in Group II were administered)

This group consists of three (3) test animals to which 1% of an aqueous solution of λ-degraded carrageenan used in Group I were orally administered as a drinking water every day, for the first 8 weeks, then 1% of an aqueous solution of λ-degraded carrageenan, containing the active ingredient used in Group II were orally administered as a drinking water every day, for the second 8 weeks.

(d) Group IV (A group of the test animals to which the drinking water used in Group I and another drinking water only containing the active ingredient were administered)

This group consists of three (3) test animals to which 1% of an aqueous solution of λ-degraded carrageenan used in Group I were orally administered as a drinking water every day, for the first 8 weeks, then further orally administered a drinking water, without containing λ-degraded carrageenan, but only containing the active ingredient in the amout of 0.1 mg/kg/day so as to be administered per one test animal in an amount of average 0.2 mg as administered to the test animals of Group II every day, for the second 8 weeks (Group II').

(e) Group V (A group of the test animals to which the drinking water used in Group II and the drinking water used in Group I were administered)

This group consists of three (3) test animals to which 1% of an aqueous solution of λ-degraded carrageenan, containing the active ingredient used in Group II were orally administered as a drinking water every day, for the first 8 weeks, then further orally administered 1% of an aqueous solution of an aqueous solution of λ-degraded carrageenan used in Group I every day, for the second 8 weeks.

(f) Group VI (A group of the test animals to which the drinking water used in Group II and another drinking water without containing λ-degraded carrageenan were administered)

This group consists of three (3) test animals to which 1% of an aqueous solution of λ-degraded carrageenan, containing the active ingredient used in Group II were orally administered as a drinking water every day, for the first 8 weeks, then further orally administered a common pure water without containing either λ-degraded carrageenan or the active ingredient, as a drinking water every day, for the second 8 weeks.

The test animals (rabbits) of Group I and Group II were killed at the time 8 weeks and 16 weeks after the beginning of the tests, and the test rabbits of Group II through Group VI were killed at the time 16 weeks after the beginning of the tests. Each of the samples of the large intestine obtained from test rabbits were examined visually and pathohistologically. The results of examinations are shown in the accompanied FIG. 1 to FIG. 6 of microscopic photographs (magnification: x40 or x100) of the samples of tissues of the large intestines obtained from test rabbits, said microscopic photographs were taken after the samples were fixed by means of formalin treatment, then dyed with hematoxylin-eosin.

Figure 2:
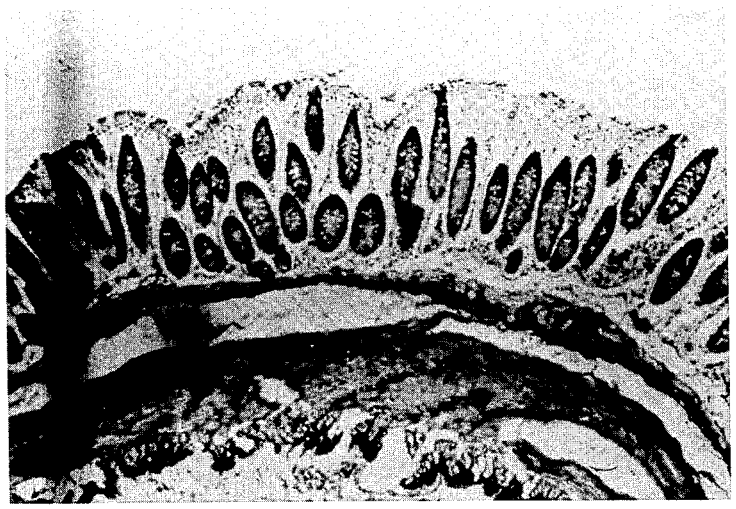
Figure 3:
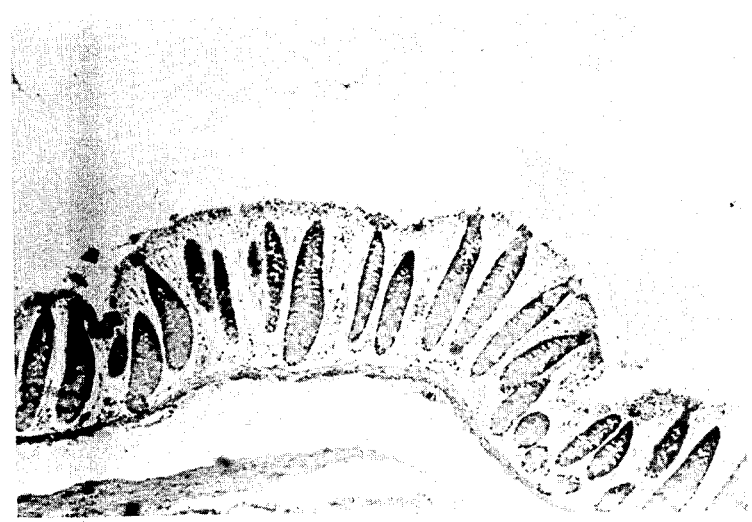
Figure 4:
Figure 5:
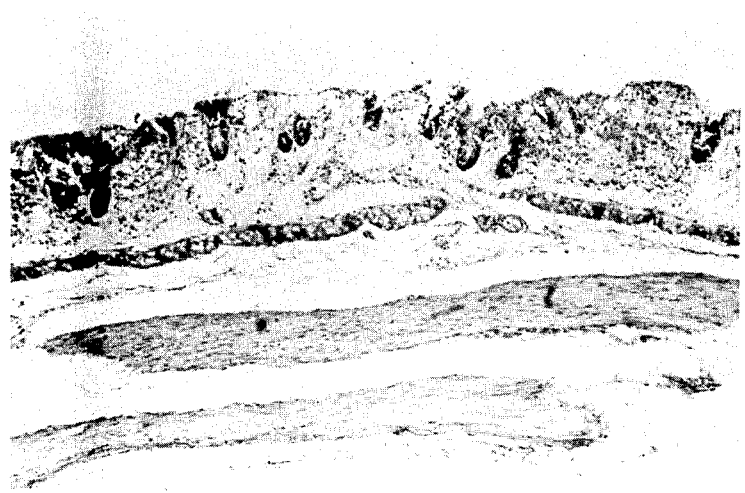
Figure 6:
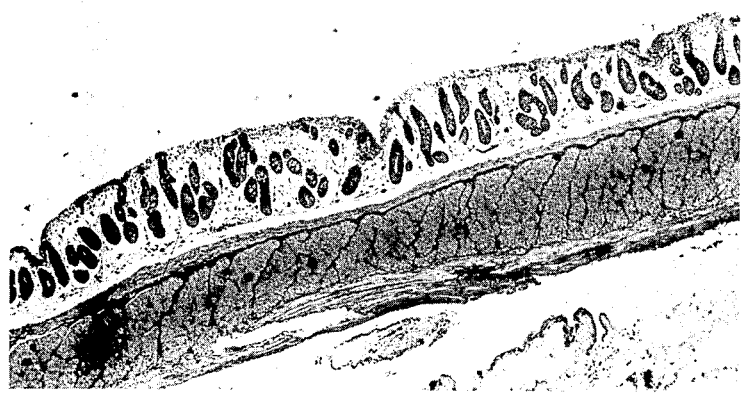

FIG. 1 shows a microscopic photograph (magnification: x40) of the sample obtained from test rabbit of Group I; FIG. 2 shows a microscopic photograph (magnification: x100) of the sample obtained from test rabbit of Group II; FIG. 3 shows a microscopic photograph (magnification: x100) of the sample obtained from test rabbit of Group III; FIG. 4 shows a microscopic photograph (magnification: x40) of the sample obtained from test rabbit of Group IV; FIG. 5 shows a microscopic photograph (magnification: x100) of the sample obtained from test rabbit of Group V; and FIG. 6 shows a microscopic photograph (magnification: x40) of the sample obtained from test rabbit of Group VI, respectively. The microscopic photograph of the sample obtained from test rabbit of Group II shown in FIG. 2 was taken at the time 8 weeks after the beginning of the test; and the remaining microscopic photographs of the samples obtianed from test rabbits of Group I and Group III through Group VI shown in FIG. 1 and FIG. 3 through FIG. 6 were taken at the time 16 weeks after the beginning of the tests, respectively.

The results of visual observations and pathohistological examinations of each of the samples of test rabbits are explained below. The pathohistological examinations were conducted according to the diagnostic evaluation standard being employed commonly in this field.

Group I

By visual observation, the sample of large intestine obtained from test rabbit of 8-weeks administration group showed diffuse erosions in the portions from the rectum to the descending colon. Particularly, edematous changes were observed in addition to the erosions appeared on the mucosa at the rectum portion. Some erosions were also observed at the part of the cecum. The sample of large intestine obtained from test rabbit of 16-weeks administration group showed the results similar to those shown by that of the test rabbit of 8-weeks administration group. However, the erosions and edematous changes were slightly decreases in 8-weeks administration group. In view of the pathohistological examination, there were observed slight ulcerative lesions, corresponding to the ulcerative rating of UL-II, on the mucosa in the portions from the rectum through the descending colon.

Severe inflammatory cellular infiltrations mainly consisting of microlymphocytes were observed on the mucosa. Crypt adscesses were also observed on the mucoderm near to the mucosomytome. Most of the mucosonoepithelial cells were defected. Among four (4) of the test rabbits, one test rabbit showed in that the mucosomytome thereof was observed with congestion. Make a comparison between the two groups, the sample of the large intestine obtained from the test rabbits of 8-weeks administration group showed remarkable pathohistological changes over those of shown by the test rabbits of 16weeks administration group.

Group II

Make a comparison between the visual observations of two groups of the samples of the large intestines obtained from test rabbits of 8-weeks administration and those of obtained from test rabbits of 16-weeks administration, there were observed not any remarkable changes between them at all. However, by conducting pathohistological examination, among three (3) test rabbits of 8-weeks administration group, the sample large intestine obtained therefrom showed a slight erosion together with localized deffects of mucosonoepithelial cells in the part of the rectum were observed. However, there was not observed any remarkable change on the mucoderm.

Similar to the results obtained from the sample of the large intestine of test rabbits of 8-weeks administration group, the only partial erosions were observed in the samples obtained from two (2) test rabbits among the three (3) test rabbits of 16-weeks administration group.

Group III

Not any remarkable changes were observed by visual observations. Similar to the results obtained from Group II, the pathohistological examinations were also the same.

Group IV

Not any remarkable changes were observed by visual observations. Also not any remarkable changes were recognized by the pathohistological examinations.

Group V

Not any remarkable changes were observed by visual observations. On the other hand, among three (3) test rabbits, two (2) rabbits showed erosions together with the defects of mucosonoepithelial cells on the mucosa of the whole large intestine by the pathohistological examinations. The portions close to the erosions, there were observed slight inflammatory cellular infiltration, such changes were shown in the portions close to the rectum, more remarkable changes were appeared.

Group VI

Not any remarkable changes were observed visually. On the other hand, among three (3) test rabbits, one (1) rabbit showed slight erosions partially at the rectum by pathohistological examination, but not any changes were observed on the mucoderm.

As can be seen from the above-mentioned explanations, the samples of large intestine obtained from the test rabbits of Group I to which only 1% of an aqueous solution of λ-degraded carrageenan were orally administered, there were observed visually in that erosions were appeared in the whole region of the large intestine and also small ulcerative pathogenic changes were observed diffusely. According to pathohistological examination, the pathogenic changes of the mucosa were atropic changes, as well as there were appeared some inflammatory cellular infiltrations and crypt abscesses, furthermore, the above-mentioned pathogenic changes were appeared in that portions close to the anus, stonger inflammatory changes were appeared. In view of these results obtained from the above-mentioned pharmacological experiments by using rabbits as the test animals, the pathogenic changes shown in the test rabbits are considered as the significant analogous models for evaluating ulcerative large intestinal diseases of human being.

According to evaluations of the active ingredients to be contained in pharmaceutical compositions of the present invention, by means of the above-mentioned pharmacological test as the significant analogous models for evaluting ulcerative large intestinal diseases, the active ingredients of the present invention possess excellent activities for the desired therapeutical purposes, thus the active ingredients to be contained in pharmaceutical compositions according to the present invention are quite useful as treating agents for curing ulcerative large intestinal diseases.

Pharmacological Test - 2

(Acute toxicity test)

Acute toxicity test of a compound prepared in Example 2 was conducted in rats by intravenous injection, the $LD_{50}$ value was 500 mg/kg.

What is claimed is:

1. A method for treating ulcerative large intestinal diseases, which comprises administering to a patient suffering from an ulcerative large intestinal disease a pharmaceutical composition containing at least one of the analogous compounds of sesquiterpene or a salt thereof represented by the formula, selected from the group consisting of the formula (1),

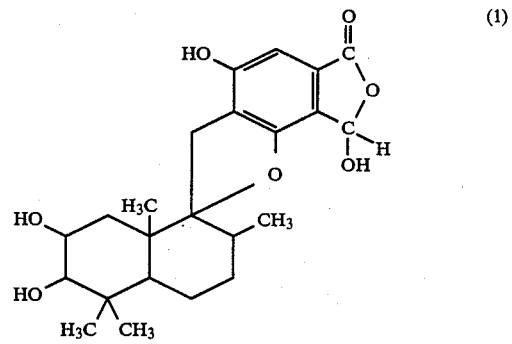

and the formula (2), (2) 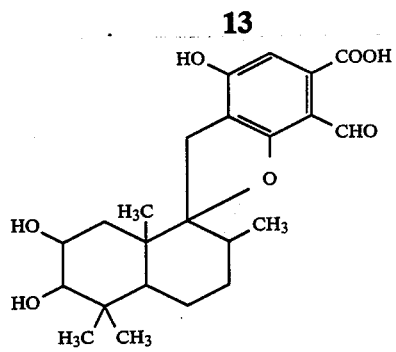
and a pharmaceutically acceptable carrier in a daily dose of from about 0.1 to 50 mg/kg of body weight/day based on the analogous compounds of sesquiterpene or a salt thereof.
2. The method of claim 1, wherein the amount of the analogous compound of sesquiterpene or a salt thereof is from about 0.5 to 30% by weight based on the entire weight of the pharmaceutical composition.
* * * * *